United States Patent [19]
Peyman

[11] Patent Number: 5,928,663
[45] Date of Patent: Jul. 27, 1999

[54] INTRAOCULAR PERFLUORCARBON COMPOSITIONS AND SURGICAL METHODS OF USING SAME

[75] Inventor: Gholam A. Peyman, New Orleans, La.

[73] Assignee: Vitrophage, Inc., Lyons, Ill.

[21] Appl. No.: 08/902,668

[22] Filed: Jul. 30, 1997

[51] Int. Cl.$^6$ ............................................. A61F 2/14
[52] U.S. Cl. ............................................. 424/427
[58] Field of Search ............................................. 414/427

[56] References Cited

U.S. PATENT DOCUMENTS 4,490,351  12/1984  Clark, Jr. ............................................. 424/5

OTHER PUBLICATIONS

Blinder, K.J., et al., Vitreon, a new perfluorocarbon, *British J of Ophth*, 75:240–244, 1991.

Chang, S., et al., Experimental vitreous replacement with perfluorotributylamine, *Am J of Ophth*, 103:29–37, Jan., 1987.

Chang, S., et al., Experimental studies of tolerance to intravitreal perfluoro–N–octane liquid, *Retina*, 11/4:367–374, 1991.

Conway, J.D., et al., Perfluorooctylbromide (PFOB) as a vitreous substitute in non–human primates, *Internat Ophth*, 17:259–264, 1993.

Eckardt, C., et al., Experimental introocular tolerance to liquid perfluotoctane and perfluropolyether, *Retina*, 11/4:375–384, 1994.

Miyamoto, K., et al., Fluorinated oils as experimental vitreous substitutes, *Arch of Ophth*, 105:1053–1056, 1986.

Miyamoto, K., et al., Perfluoroether liquid as a long–term vitreous substitute, *Retina*, 4/4:264–268, 1984.

Nibih, M., et al., Experimental evaluation of perfluorophenanthrene as a high specific gravity vitreous substitute: a preliminary report, *Ophth Surg*, 20/4:286–293, Apr. 1989.

Peyman, G.A., et al., Long–term vitreous replacement in primates with intravitreal vitreon or vitreon plus silicone, *Ophth Surg*, 22:657–664, 1991.

Refojo, M.F., et al., The refractive index of Vitreon, *Ophth Surg*, (letter to the editor), 23/6:436, Jun. 1992.

Schulman, J.A., et al., Management of giant retinal tears with perfluoroperhydrophenanthrene (Vitreon) *Jpn J Ophthalmol*, 37:70–77, 1993.

Sparrow, J.R., et al., Retinal tolerance to intravitreal perfluoroethylcyclohexane liquid in the rabbit, *Retina*, 13/1:56–62, 1993.

Tanji, T.M., et al., Perfluoroperhydrophenanthrene (Vitreon) as a short–term vitreous substitute after complex vitreoretinal surgery, *Ophth Surg*, 24/10:681–685, Oct. 1993.

Velikay, M., et al., Experimental long–term vitreous repolacement with purified and nonpurified perfluorodecalin, *Am J of Ophth*, 116:565–570, Nov. 1993.

Primary Examiner—Carlos A. Azpuru
Attorney, Agent, or Firm—Wood,Herron & Evans,L.L.P.

[57] ABSTRACT

Mixtures of perfluorocarbon liquids having an index of refraction different than water enable their visualization for use in intraocular surgery. These mixtures are used in the surgical repair retinal tears or detachments. Mixtures of perfluoroperhydrophenanthrene and perflurooctane or perfluorooctyl bromide are preferably used.

17 Claims, 1 Drawing Sheet

INTRAOCULAR PERFLUORCARBON COMPOSITIONS AND SURGICAL METHODS OF USING SAME

FIELD OF THE INVENTION

This invention relates to the use of perfluorocarbon liquid mixtures and to their use in intraocular surgical methods.

BACKGROUND OF THE INVENTION

The eye is comprised of many complex components including the cornea, vitreous, aqueous humor, retina and lens. Each component has a distinct function and each is susceptible to disorders which can reduce the quality of vision and/or result in partial or total blindness. Such disorders include vitreous liquefaction and opacification, retinal detachment, dislocation of the lens, glaucoma and opacification of the lens and cornea.

Retinal detachment is the leading cause of blindness in the United States. The most important factor contributing to retinal detachment is liquefaction and shrinkage of the vitreous of the eye. The vitreous is a gel which fills the posterior chamber of the eye between the retina and the lens. The vitreous functions to give shape to the eye and to support the retina against the choroidal tissues. As an individual ages or in some ocular disorders, this gel may liquefy and pull away from the retina. This shrinking of the vitreous may lead to retinal tearing with or without retinal detachment.

Several methods have been used for treatment of retinal tears and detachment. In less complicated cases retinal detachment is treated with a surgical procedure known as scleral buckling. During this procedure the retinal tear is supported externally by a silicone element which is sutured to the wall of the eye causing an indentation which provides support for the detached or torn retina. In more severe forms of retinal detachment or conditions which requires special considerations other methods are used. For example, retinal detachment may be accompanied by proliferation of abnormal tissue on the surface of the retina resulting in traction on the surfaces of the retina which prevents reattachment by scleral buckling. Another condition for which treatment with scleral buckling is often unsuccessful is a giant retinal tear in which a large tear in the peripheral retina extends for more than 90 degrees of the eye's circumference.

In one approach to the treatment of complicated cases of retinal reattachment the vitreous is removed surgically and replaced by a balanced saline solution. After removal of any membranes on the surface of the retina, sterile air (the procedure favored most in the United States) or silicone oil (the procedure favored most in Europe), is injected into the posterior chamber of the eye to flatten the retina against the choroidal tissues. As both of these vitreous substitutes have lower specific gravity than water, they tend to float on water and fill the superior portion of the eye. Most retinal tears occur in the peripheral portion of the eye which necessitates that the patient to lie face down while the physician introduces an air bubble into the posterior chamber in order to force the detached retina back against the choroid. Maintaining the patient in a face-down position is inconvenient for the patient and physician and increases both the risk of contaminating the operative field and the anesthetic risk. In addition, at the completion of surgery a gas bubble or silicone oil is left in the eye to provide an internal tamponade force holding the retina in place while laser or cryotherapy scars are formed by the surgeon to provide a permanent chorioretinal adhesion. Thus the patient must continue to lie face down for a recovery period which may extend to several days. Silicone oil also has the disadvantage of high viscosity which makes it less suitable for introduction through microsurgical instruments.

Because of the disadvantages and limitations of the previously described methods, researchers have investigated alternative treatments including the use of perfluorocarbon liquids (PFCs). PFCs were initially investigated as long term replacements of the vitreous because they have physical properties similar to the vitreous, for example, transparency, consistency, refractive indices, high solubilities for oxygen and carbon dioxide and immiscibility with blood and water. Subsequent research has indicated that these compounds are not suitable for long term replacement because they are toxic to eye tissue. However, U.S. Pat. No. 4,490,351, issued to Clark in 1984, discloses the use of PFCs during surgery for the treatment of retinal tears or detachments because perfluorocarbon liquids have a density greater than vitreous, unlike air or silicone oil, and can be introduced into the vitreous cavity while the patient is lying face-up. The dense liquid sinks to the retinal surface, displacing preretinal and subretinal fluid while flattening the retina, thus enabling retinal reattachment. The heavier than water property of the PFC allows it to function as an intraocular tool in repositioning the retina and unfolding an inverted flap in eyes with giant retinal tears, with a minimal amount of intraocular manipulation. This method also has an advantage over those using gas or silicone oil since the patient can be treated while lying face up and the physician can operate in a standing or sitting position.

Following surgery, the PFC is replaced with a vitreous substitute or is left in the eye to provide a postoperative tamponade until chorioretinal scars develop sufficiently to maintain the reattached retina. Subsequently, the PFC is removed by aspiration followed by, or concurrently with, the introduction of a sterile gas bubble or silicone oil. During this PFC-air or PFC-oil exchange, the meniscus flattens, resulting in a thin flat layer of residual PFC which is difficult to remove. Removal of the PFC is accomplished by adding a small amount of saline solution to the remaining PFC. The PFC, being immiscible with water, forms into droplets or bubbles permitting aspiration of the PFC from the vitreous cavity. Because of the demonstrated toxicity of PFC when left in the eye long-term, it is important that it be completely removed after surgery or postoperative use. To insure complete removal of the PFC multiple washings with saline may be necessary.

PFCs have also been useful for removal of a dislocated lens. The lens of the eye may become dislocated as a result of trauma or disease and lenses dislocated into the vitreous cavity may interfere with vision or be associated with a retinal detachment. In these situations the lens is removed with vitrectomy techniques. PFCs have been used as an intraoperative tool during vitreoretinal surgery to remove dislocated lenses. Placement of liquid PFC in the vitreous after vitrectomy serves to float the lens material off the retina, aid in reattaching the retina in cases in which it is detached, and provide a cushion that prevents dropped fragments of lens from traumatizing the retina. After lens removal the PFC is removed as for vitreoretinal surgery.

PFCs have gained increased usage in complex vitreoretinal surgery. However, due to their long term toxicity to eye tissue they must be completely removed after surgery. *Retina:* "Perfluoroether liquid as a long-term vitreous substitute: an experimental study." by K. Miyamoto, M. F. Refojo, F. I. Tolentino, G. A. Fournier and D. M. Albert 4:264–268, 1984. *American Journal of Ophthalmology:*

"Experimental vitreous replacement with perfluorotributylamine." by S. Chang, N. J. Zimmerman, T. Twamoto, R. Oritiz and D. Faris 103: 29–37, 1987. *Archives of Ophthalmology:* "Fluorinated oils as experimental vitreous substitutes." by K. Miyamoto, M. F. Refojo, F. I. Tolentino, G. A. Fournier and D. M. Albert. 105: 1053–1056, 1986. The short term postoperative use of PFCs has shown promise, but with the exception of perfluoroperhydrophenanthrene (F-phenanthrene), PFCs have shown short term toxicity to the eye which has limited their use. *Ophthalmic Surgery:* "Experimental evaluation of perfluorophenanthrene as a high specific gravity vitreous substitute." by M. Nabih, G. A. Peyman, L. C. Clark, R. E. Hoffmann, M. Mceli, M. Abou-Streit, M. Tawakol and K. R. Liu. 20: 286, 1989. F-phenanthrene has been shown to be well tolerated for short periods of time enabling its postoperative use, but the disadvantage of F-phenanthrene has been its index of refraction, which is similar to that of water, which makes it invisible in a clear saline solution thus making removal of residual F-phenanthrene very difficult. *Ophthalmic Surgery:* "The Refractive Index of Vitreon." (letter to the editor) by M. F. Refojo, J. Araiz, and M. Arroyo, F. I. Tolentino. 23: 436, 1992.

SUMMARY OF THE INVENTION

This invention is directed to opthalmologically compatible mixtures of liquid perfluorocarbons, modified to have a refractive index different than water, and methods for the treatment of opthalmological disorders using these mixtures. For example these liquid mixtures can be used for the treatment of intraocular disorders which include a detached or torn retina and a dislocated lens.

Many combinations of PFCs may be suitable for use in intraocular surgery when modified in this way. A preferred composition comprises about 5–95% (v/v) perfluoroperhydrophenanthrene (F-phenanthrene) and about 5–95% of other perfluorocarbon compounds(s). The viscosity of the mixture is preferably greater than the viscosity of water in order to prevent migration of the composition into the subretinal space. In one form of the opthalmologically compatible composition, a well tolerated perfluorocarbon, which is not visible in saline, has been modified to be visible. In this preferred composition, F-phenanthrene which is well tolerated in the eye, but is not visibly distinguishable from water, becomes visible when homogeneously mixed with perfluorooctane (F-octane) or perfluorooctylbromide (F-octylbromide). The refractive index of F-phenanthrene (1.33) which is nearly identical with water (1.33) is modified to about 1.30–1.32 when homogeneously mixed with F-octane or F-octylbromide. To modify the index of refraction to be different than that of water the percent of F-phenanthrene in the mixture is about 5–95% (v/v) and the percent of F-octane or F-octylbromide is about 5–95%.

In addition, it has been found that such mixtures have other unexpected beneficial effects. The preferred mixtures have a vapor pressure less than about 50 torr which contributes to these mixtures being more tissue friendly and less likely to emulsify in the eye. For example, F-octane alone is not tolerated inside the eye because of its toxicity and high vapor pressure, whereas the mixture of F-phenanthrene and F-octane has a lower vapor pressure than F-octane and is well tolerated, showing no toxicity to the eye. Furthermore, the mixture also provides a change in the viscosity of the F-octane. F-octane has a low viscosity (0.9 cs) which makes it easier to penetrate a retinal tear and migrate into the subretinal space, which is very undesirable during surgery. The homogeneous mixture of F-octane with F-phenanthrene has a higher viscosity than water, thus improving on the characteristics of the F-octane. Yet the viscosity is still low enough to be transferred readily through microsurgical instruments.

These perfluorocarbon mixtures can be used for the treatment of intraocular disorders including a detached or torn retina and a dislocated lens. The method for repairing the intraocular disorder involves introducing the PFC mixture into the eye, repair of the intraocular disorder and exchange of the PFC with an aqueous medium. Because most PFCs have toxic effects when left long term in the eye, it is important that the PFCs be completely removed following surgery. PFC mixtures modified to have an index of refraction different than water ensure complete removal because visual confirmation that no PFC bubbles remain in the aqueous medium is possible.

Other advantages and embodiments will be understood with reference to the following drawings and detailed description.

DETAILED DESCRIPTION OF THE INVENTION

F-phenanthrene, as part of a homogeneous mixture of fluorocarbons having an index of refraction different than water (1.33), is used as a vitreous substitute during intraocular surgery for the treatment of intraocular disorders. For purposes of this application homogeneous means the mixture is in a single liquid phase. The preferred compositions, as shown by Table 1, Examples 1–5, are mixtures of F-phenanthrene and F-octane or F-octylbromide in order to obtain the advantages of visibility for removal, tolerability in the eye and viscosity to avoid undesirable migration, as developed above.

TABLE 1

| Example | Composition | Refractive Index at 20° C. |
|---|---|---|
| 1 | 100% F-phenanthrene | 1.3338 |
| 2 | 75% F-phenanthrene, 25% F-octylbromide | 1.3274 |
| 3 | 75% F-phenanthrene, 25% F-octane | 1.3191 |
| 4 | 50% F-phenanthrene, 50% F-octylbromide | 1.3200 |
| 5 | 50% F-phenanthrene, 50% F-octane | 1.3026 |

The perfluorocarbon may also be selected from a group consisting of consisting of perfluoro-n-octane (perfluorooctane), perfluorooctylbromide, perfluorotributylamine, perfluorodecalin, perfluoropolyethers, perfluoroethylcyclohexane, perfluorotri-n-propylamine, perfluoropolyether, perfluorotetramethylcyclohexane and mixtures thereof.

Figure 1:
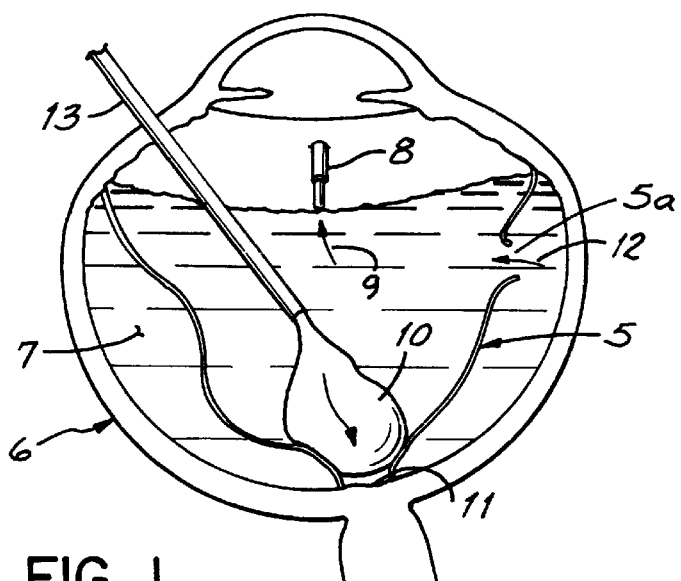
FIGS. 1 and 2 are schematic cross-sectional views of the showing the introduction of perfluorocarbon liquid into the vitreous cavity of the eye with partial air-fluid exchange during the injection process.
Figure 2:
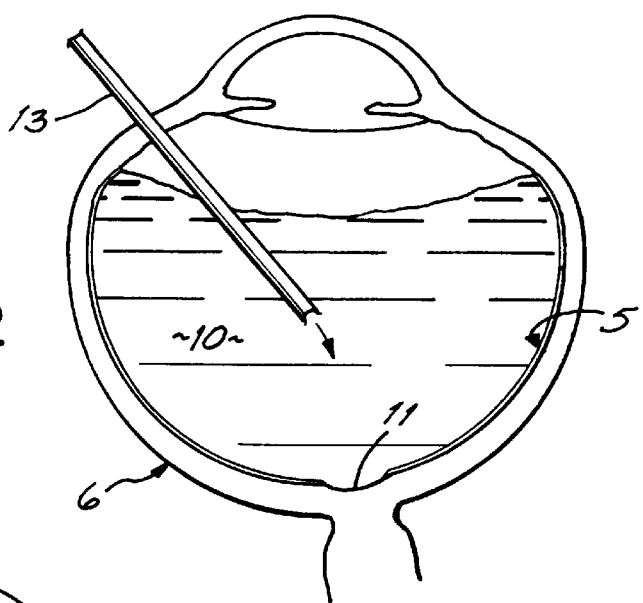
Figure 3:
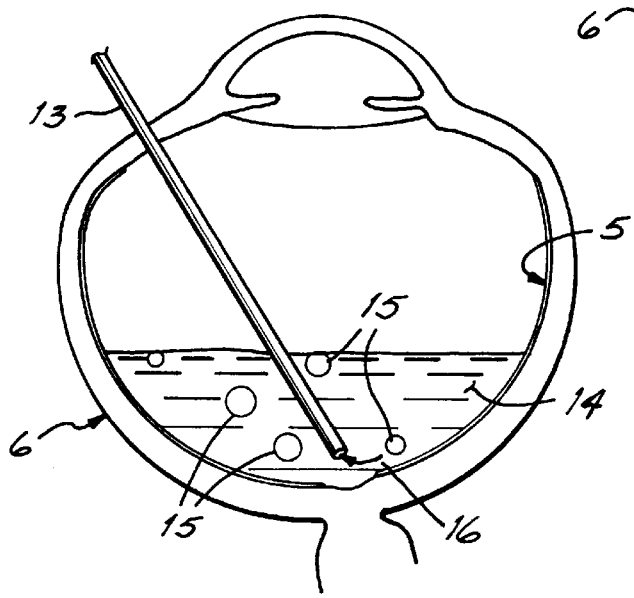
FIG. 3 is similar to FIGS. 1 and 2 but shows fluid washing to remove remaining perfluorocarbon liquid.

FIGS. 1 and 2 show the surgical technique for treatment of a torn or detached retina 5 of the eye 6. This technique involves a conventional three-port pars plana approach (two ports shown) and removal of the vitreous gel 7 with the vitrectomy instrument 8, as shown by the arrow 9. The perfluorocarbon mixture 10 of Examples 2–5 is injected over the optic disc 11 at the back of the eye 6 with a partial air-fluid exchange. The PFC 10 is injected slowly to allow displacement of the subretinal fluid anteriorly through a retinal tear 5a, as shown by the arrow 12. Epiretinal membrane peeling and retinotomies are performed as needed, allowing the retina 5 to be flattened. As shown in FIG. 2, the posterior cavity is then filled with PFC 10 to flatten the retina 5. Endophotocoagulation and/or transscleral cryopexy, under the PFC 10, is used at the end of the operation when the retina 5 is completely flat. Modifications to the procedure are made for the eyes with suprachoroidal hemorrhage and dislocated intraocular lenses. The perfluorocarbon mixture is removed following surgery or can be left in the eye postoperatively until chorioretinal scars are considered sufficient to maintain a flat retina or postoperative complications necessitate its removal. As shown in FIG. 3, PFC 10 removal is by a three-port pars plana air-fluid exchange (two ports shown), using an extrusion needle 13 to evacuate the majority of the PFC. In order to remove the remaining PFC, a fluid wash is performed as shown in FIG. 3. Physiologic saline 14 is introduced by air-fluid exchange. Because the PFC is immiscible with water, it forms droplets or bubbles 15. These bubbles 15 are readily visible because the index of refraction of the PFC differs from that of the saline solution 14 and the remaining perfluorocarbon bubbles are removed by aspiration through the extrusion needle 13, as shown by the arrow 16. The saline solution 14 is then replaced with a suitable long-term vitreous replacement.

Similarly, a dislocated lens may be treated; after vitrectomy and replacement of the vitreous with the PFC mixture of Examples 2–5, the lens is floated off the retina and into the anterior vitreous cavity. If necessary the lens is fragmented while floating on the PFC. The lens fragments are then removed by aspiration. Following lens removal the PFC is removed as above.

Other variations or embodiments of this invention will become apparent to one of ordinary skill in the art in view of the above drawings and description, and the forgoing embodiments are not to be construed as limiting the scope of this invention.

What is claimed is:

1. An opthalmologically compatible composition for intraocular surgical use consisting essentially of a homogeneous mixture of perfluorocarbons having a refractive index different than water.

2. The composition of claim 1 where the viscosity of the mixture is greater than the viscosity of water to prevent migration of the composition into the subretinal space.

3. The composition of claim 2 where the vapor pressure is less than 50 torr.

4. The composition of claim 1 where one of the perfluorocarbons is perfluoroperhydrophenanthrene.

5. The composition of claim 4 where a second perfluorocarbon is selected from a group consisting of perfluoro-n-octane (perfluorooctane), perfluorooctylbromide, perfluorotributylamine, perfluorodecalin, perfluoropolyethers, perfluoroethylcyclohexane, perfluorotri-n-propylamine, perfluoropolyether, perfluorotetramethylcyclohexane and mixtures thereof.

6. The composition of claim 4 where a second perfluorcarbon is selected from a group consisting of perfluoro-n-octane (perfluorooctane) and perfluorooctylbromide to modify the refractive index of the mixture.

7. The composition of claim 5 where the percent (v/v) of perfluoroperhydrophenanthrene in the mixture is 5–95% and the remaining perfluorocarbon compound(s) is 5–95%.

8. An opthalmologically compatible composition for intraocular surgical use comprising a mixture of perfluorocarbons wherein the percent (v/v) of perfluoroperhydrophenanthrene is 5–95% and the percent (v/v) of a second perfluorocarbon is 5–95% and this second perfluorocarbon is selected from a group consisting of perfluoro-n-octane (perfluorooctane) and perfluorooctylbromide to modify the refractive index of the mixture.

9. A surgical method of repairing an intraocular disorder of an eye comprising introducing into the intraocular structure under treatment a liquid comprising a perfluorocarbon mixture having a refractive index different than water, repairing the intraocular disorder, exchanging the liquid perfluorocarbon with an aqueous medium, visualizing the difference in the index of refraction between the perfluorocarbon and the aqueous medium to facilitate the exchange of the perfluorocarbon.

10. The method of claim 9 where the intraocular disorder is a detached or torn retina and comprising the further steps of removing the vitreous of the eye, introducing the perfluorocarbon mixture, repairing the retina, exchanging the perfluorocarbon with saline.

11. The method of claim 9 where the intraocular disorder is a dislocated lens and comprising the further steps of removing the vitreous of the eye, floating the lens off the retina, removing the lens, exchanging the perfluorocarbon with saline.

12. The method of claim 9 where the perfluorocarbon mixture includes perfluoroperhydrophenanthrene.

13. The method of claim 12 where a second perfluorocarbon is selected from a group consisting of perfluoro-n-octane (perfluorooctane), perfluorooctylbromide, perfluorotributylamine, perfluorodecalin, perfluoropolyethers, perfluoroethylcyclohexane, perfluorotri-n-propylamine, perfluoropolyether, perfluorotetramethylcyclohexane and mixtures thereof.

14. The method of claim 12 where a second perfluorcarbon is selected from a group consisting of perfluoro-n-octane (perfluorooctane) and perfluorooctylbromide to modify the refractive index of the mixture.

15. The method of claim 14 wherein the percent (v/v) of perfluoroperhydrophenanthrene in the mixture is 5–95% and the remaining perfluorocarbon compound(s) is 5–95%.

16. The method of claim 15 where the intraocular disorder is a detached or torn retina and comprising the further steps of removing the vitreous of the eye, introducing the perfluorocarbon mixture, repairing the retina, exchanging the perfluorocarbon with saline.

17. The method of claim 15 where the intraocular disorder is a dislocated lens and comprising the further steps of removing the vitreous of the eye, floating the lens off the retina, removing the lens, exchanging the perfluorocarbon with saline.

* * * * *